United States Patent [19]
Swan

[11] Patent Number: 6,019,600
[45] Date of Patent: Feb. 1, 2000

[54] AUTOCLAVABLE ABRASION RESISTANT MIRROR

[75] Inventor: Jawn P. Swan, Los Angeles, Calif.

[73] Assignee: Crystalmark Dental Systems, Inc., Glendale, Calif.

[21] Appl. No.: 09/219,555

[22] Filed: Dec. 22, 1998

[51] Int. Cl.⁷ ..................................................... A61B 1/24
[52] U.S. Cl. ..................... 433/30; 359/360; 359/359
[58] Field of Search ..................... 433/30, 31; 359/359, 359/360, 584, 585, 589, 883, 884

[56] References Cited

U.S. PATENT DOCUMENTS

| | | | |
|---|---|---|---|
| 2,427,592 | 9/1947 | Dimmick | 88/105 |
| 4,294,356 | 10/1981 | Abramowitz | 433/30 X |
| 5,216,551 | 6/1993 | Fujii | 359/884 |
| 5,269,683 | 12/1993 | Hickok et al. | 433/30 |
| 5,751,474 | 5/1998 | Hohenegger et al. | 359/360 |
| 5,906,487 | 5/1999 | Carr | 433/30 |

OTHER PUBLICATIONS

CRA Clinical Research Associates Newsletter, vol. 21, Issue 12, Dec. 1997.

*Primary Examiner*—Nicholas D. Lucchesi
*Attorney, Agent, or Firm*—Sheldon & Mak

[57] ABSTRACT

An autoclavable, abrasion resistant dental mirror comprises a holder and a mirror element mounted in the holder. The mirror element comprises a sapphire body, an optically reflective aluminum layer on the rear surface of the sapphire body, and a protective layer on the reflective layer.

11 Claims, 1 Drawing Sheet

AUTOCLAVABLE ABRASION RESISTANT MIRROR

BACKGROUND

Dental surgery techniques continually advance. One technique that is quickly being adopted is air abrasion cavity preparation. In this technique, small particles of aluminum oxide ($Al_2O_3$), typically between 17 to 50 microns in size, are used, under air pressure, for removal of incipient decay. Among the advantages of this technique are that it allows removal of decay without the need for anesthetic, without the attendant residual anesthetic numbness. Moreover, it is available for patients who are sensitive to anesthetics. Moreover, air abrasion cavity preparation eliminates noise, odor, vibration, and the negative psychological connotations associated with the typical dental handpiece.

A problem with air abrasion is the wear and tear on conventional dental mirrors. The aluminum oxide particles adversely affect the reflective integrity of the conventional dental mirror, requiring their constant replacement, which is expensive for the dentist, thereby raising the cost of dental care.

Accordingly, there is a need for dental mirrors that can be used with air abrasion caries removal systems. Moreover, it is necessary that the mirror be sterilized between uses to avoid cross infection of patients. The equipment in most dental offices for sterilization is an autoclave. Accordingly, there is need for a dental mirror that is not only abrasion resistant, but also autoclavable multiple times, and preferably at least 50 times.

SUMMARY

The present invention is directed to a dental mirror that satisfies this need. The mirror comprises a holder and a mirror element. Preferably the holder is exactly the type currently used by dentists, and thus comprises a handle and a frame having side walls and an open front. A mirror element is mounted in the frame. The mirror element comprises a sapphire body having a front surface and a rear surface with the front surface facing the open front of the frame. The sapphire body is provided with an optically reflective aluminum layer on its rear surface. A protective layer is provided on the reflective layer. The protective layer is sufficiently thick that the mirror can be autoclaved at least 50 times at 270° F. for 15 minutes with steam, and maintain its structural integrity. Typically the protective layer is aluminum oxide.

It has been found that this combination of a sapphire body and aluminum reflective layer, and a protective layer, which is preferably aluminum oxide, provides a abrasion resistant, autoclavable mirror.

DRAWINGS

These and other features, aspects and advantages of the present invention will become better understood from the following description, appended claims, and accompanying drawings where:

DESCRIPTION

Figure 1:
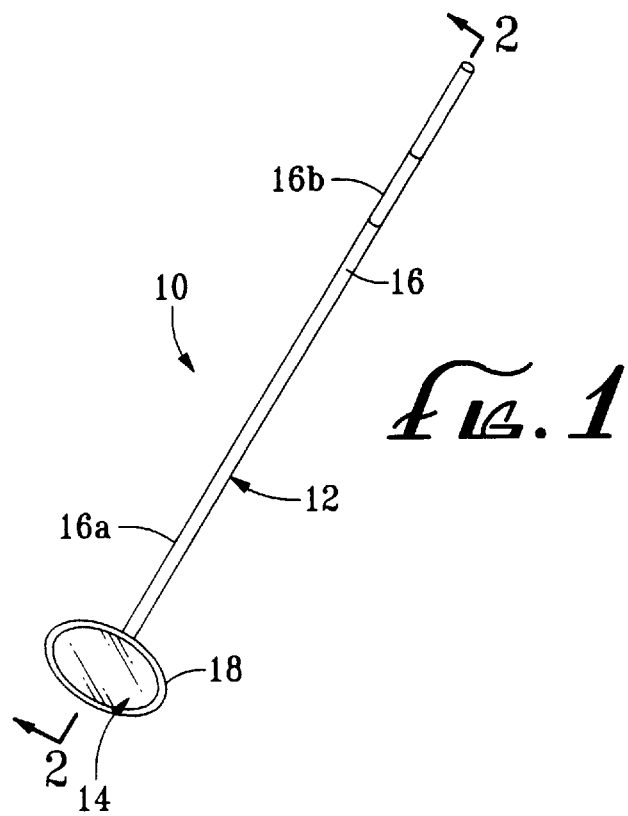
FIG. 1 is a perspective view of a dental mirror according to the present invention.
Figure 2:
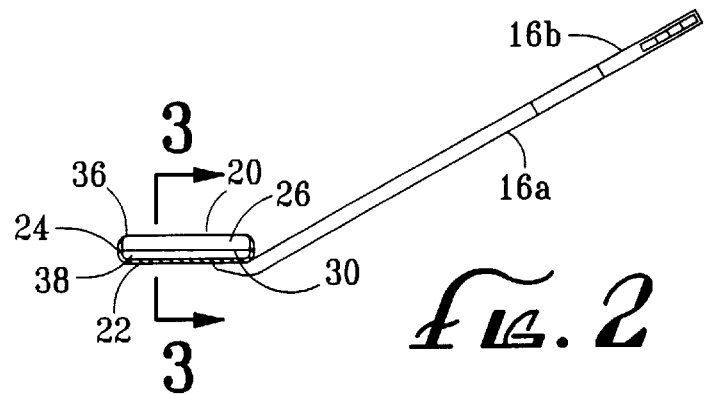
FIG. 2 is a sectional view of the dental mirror of FIG. 1 taken on line 2—2 of FIG. 1.
Figure 3:
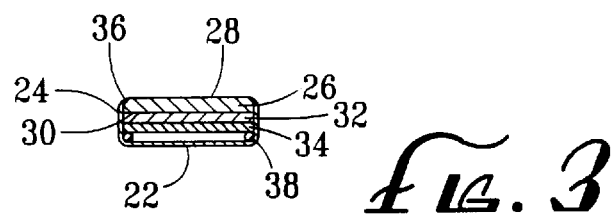
FIG. 3 is a sectional view of the mirror element of the mirror of FIG. 1, showing the multiple layers.

With reference to the drawings, a dental mirror 10 embodying features of the present invention comprises a holder or housing 12 and a mirror element 14. Preferably the holder 12 is of the type conventionally used with dental mirrors, and is formed of stainless steel. It comprises a handle 16 and a frame 18, also referred to as a can. The frame 18 comprises an open front 20, a rear wall 22, and a circumferential side wall 24. As shown in FIG. 1, preferably the frame 18 is round in a top plan view. Typically, the handle 16 is provided in two sections, a section 16a welded or otherwise permanently secured to the frame 18, and a handpiece section 16b. The two sections 16a and 16b are threaded together.

The mirror element 14 comprises a sapphire body 26, substantially optically transparent, having a front surface 28 and a rear surface 30. Sapphire is crystalline aluminum oxide ($Al_2O_3$). The mirror element 14 is mounted in the frame 18 with its front surface 28 facing forwardly towards the open front 20 so that reflections can be seen in the mirror element 14.

On the rear surface 30 of the sapphire body 26 is provided a reflective layer 32, typically aluminum, and on the reflective layer 32, a protective layer 34, typically aluminum oxide.

The sapphire body 26 is typically from about 5 to about 100 mils thick, and preferably about 50 mils thick.

The peripheral edge 36 of the sapphire body 26 is chamfered by about 50° and the side wall 24 of the frame 18 is swaged over the chamfered edge 36 to hold the mirror element 14 in the frame 18. A silicone O-ring 38 is positioned between the rear surface of the mirror element 14, i.e., against the protective layer 34 and the rear wall 22 of the frame 18. The O-ring 38 holds the mirror element 14 spaced apart from the rear wall 22 of the frame 18. A satisfactory O-ring can be obtained from Apple Rubber Products, Inc. of Lancaster, N.Y., under the name "MicrOring."

Preferably the reflective aluminum layer is from about 1000 to about 3000 angstroms (Å) thick, a thickness sufficient to give good reflectivity with minimum pin holes. Thicknesses greater than a 1000 angstroms do not improve the reflectivity, but do increase the cost of the product.

Similarly, the protective layer is from about 1000 to about 3000 angstroms thick. It needs to be sufficiently thick that the mirror can be autoclaved at least 50 times at 270° F. for 15 minutes with steam to satisfy the commercial requirement of dentists. If it is too thin, the mirror will not satisfy this requirement. Thicknesses greater than 3000 angstroms do not significantly improve functionality, but do increase the manufacturing costs.

The abrasion resistant property of the product is provided by the sapphire body, which is highly resistant to abrasion by the aluminum oxide particles used in air abrasion dentistry. I believe the autoclavability feature results from the selection of aluminum as the reflective layer, the aluminum being compatible with the sapphire body. I also believe the protective layer contributes to autoclavability, and the selection of aluminum oxide, which is believed to be compatible with the aluminum reflective layer, also contributes to the autoclavability. However, my belief as to why my product is successful has not yet been scientifically demonstrated, and in fact, lot to lot variations in the product have been noted, where some lots do not satisfy the autoclavability requirements on the product.

The current preferred method for manufacturing the product is a vacuum vapor deposition technique. In particular, sapphire bodies are placed in a fixture and the layers are deposited on the sapphire body under vacuum. Before being placed on the fixture the layers are cleaned with a caustic cleaning product such as Alcanox™, tap water, distilled water, isopropyl alcohol, and other materials conventionally used in the trade for removing contaminants and oils.

Before coating, the sapphire substrate undergoes an argon ion etch. The layers are deposited under vacuum, with a typical minimum base pressure of $5\times10^{-5}$ torr, with the coating beginning after a 2 to 3 hour pump and heat cycle.

Vacuum vapor deposition utilizing electron beam evaporation has been successfully performed by Tribo Coating of Malibu, Calif., utilizing their process #214.

It has been found that dental mirrors prepared according to this method meet the needs of dentists. The dental mirrors have been found to be highly resistant to abrasion in air abrasion dental procedures, and autoclavable multiple times, to render them economical for use on multiple patients.

Although the present invention has been described in considerable detail with reference to certain preferred versions thereof, other versions are possible. For example, the mirror element can be formed in a shape to provide a magnification feature. Moreover, the mirror need not be round in configuration. Also, the mirror element can be used for applications other than dental mirrors, such as for conventional surgery where it is necessary to visualize a person's internal anatomy. Accordingly, the scope of the present invention should not be limited to the description of the preferred versions contained herein.

All features disclosed in the specification, including the claims, abstracts, and drawings, and all the steps in any method or process disclosed, may be combined in any combination, except combinations where at least some of such features and/or steps are mutually exclusive. Each feature disclosed in the specification, including the claims, abstract, and drawings, can be replaced by alternative features serving the same, equivalent or similar purpose, unless expressly stated otherwise. Thus, unless expressly stated otherwise, each feature disclosed is one example only of a generic series of equivalent or similar features.

What is claimed is:

1. An autoclavable, abrasion resistant dental mirror comprising:
   a) a holder comprising a handle and a frame having side walls and an open front; and
   b) a mirror element mounted in the frame, the mirror element comprising:
      (i) a sapphire body having a front surface and a rear surface with the front surface facing the open front of the frame;
      (ii) an optically reflective aluminum layer on the rear surface of the sapphire body; and
      (iii) a protective layer on the reflective layer, the protective layer being sufficiently thick that the mirror can be autoclaved at least 50 times at 270° F. for 15 minutes with steam.

2. The mirror of claim 1 wherein the frame has a rear wall, and the mirror includes an O-ring maintain the mirror element space apart from the frame rear wall.

3. The mirror of claim 1 wherein the protective layer is aluminum oxide.

4. The mirror of claim 1 wherein the sapphire body is from about 5 to about 100 mils thick.

5. The mirror of claim 1 wherein the aluminum layer is formed by vapor vacuum deposition.

6. The mirror of claim 1 wherein the protective layer is formed by vapor vacuum deposition.

7. A dental method comprising:
   a) selecting an abrasion resistant, autoclavable dental mirror comprising:
      i) a holder comprising a handle and a frame having side walls and an open front; and
      ii) a mirror element mounted in the frame, the mirror element comprising:
         (A) a sapphire body having a front surface and a rear surface with the front surface facing the open front of the frame;
         (B) an optically reflective on the rear surface of the sapphire body; and
         (C) a protective layer on the reflective layer, the protective layer being sufficiently thick that the mirror can be autoclaved at least 50 times at 270° F. for 15 minutes with steam;
   b) placing the dental mirror in the mouth of a patient while treating the patient with abrasive particles; and
      i) after step b) and before using the dental mirror with another patient, sterilizing the dental mirror by autoclaving it at an elevated temperature with steam; and
   repeating steps (B) and (C) at least 50 times with the same dental mirror.

8. An autoclavable, abrasion resistant mirror comprising:
   a) a sapphire body having a front surface and a rear surface;
   b) an optically reflective aluminum layer on the rear surface of the sapphire body; and
   c) a protective layer on the reflective layer, the protective layer being sufficiently thick that the mirror can be autoclaved at least 50 times at 270° F. for 15 minutes with steam.

9. The mirror of claim 8 wherein the protective layer is aluminum oxide.

10. The mirror of claim 8 wherein the sapphire body is from about 5 to about 100 mils thick.

11. An autoclavable, abrasion resistant dental mirror comprising:
    a) a holder comprising a handle and a frame having side walls, an open front, and a rear wall;
    b) a mirror element mounted in the frame, the mirror element comprising:
       (i) a sapphire body having a front surface and a rear surface with the front surface facing the open front of the frame;
       (ii) an optically reflective aluminum layer on the rear surface of the sapphire body, the aluminum layer being formed by vapor vacuum deposition;
       (iii) an aluminum oxide protective layer on the reflective layer, the protective layer being sufficiently thick that the mirror can be autoclaved at least 50 times at 270° F. for 15 minutes with steam, the aluminum oxide layer being formed by vacuum vapor deposition; and
    c) a silicone O-ring maintaining the mirror element spaced apart from the frame rear wall.

* * * * *